United States Patent [19]
Park et al.

[11] Patent Number: 5,924,992
[45] Date of Patent: Jul. 20, 1999

[54] SEMI-COMPLIANT NEEDLE GUIDE FOR USE WITH ULTRASOUND TRANSDUCERS

[75] Inventors: William J. Park, San Jose; Randal J. Bertuccelli, Mount Aukum, both of Calif.; Robert Mesaros, Bozeman, Mont.; Brian S. MacInnes, Saratoga, Calif.; Richard W. Henderson, Fremont, Calif.; Kathleen A. Ruvolo, Mill Valley, Calif.; Richard Lyon, Palo Alto, Calif.; Nancy A. Cheadle, Saratoga, Calif.; John William Sliwa, Jr., Los Altos, Calif.

[73] Assignee: Acuson Corporation, Mountain View, Calif.

[21] Appl. No.: 08/980,979

[22] Filed: Nov. 26, 1997

[51] Int. Cl.$^6$ .................................................. A61B 8/00
[52] U.S. Cl. ............................................................ 600/461
[58] Field of Search .................................. 600/461, 437, 600/459, 462

[56] References Cited

U.S. PATENT DOCUMENTS

| | | |
|---|---|---|
| 4,576,175 | 3/1986 | Epstein . |
| 4,898,178 | 2/1990 | Wedel . |
| 4,899,756 | 2/1990 | Sonek ...................................... 600/461 |
| 5,052,396 | 10/1991 | Wedel et al. . |
| 5,076,279 | 12/1991 | Arenson et al. ......................... 600/461 |
| 5,623,931 | 4/1997 | Wung et al. ............................. 600/461 |
| 5,758,650 | 6/1998 | Miller et al. ............................. 600/461 |

*Primary Examiner*—Brian L. Casler
*Assistant Examiner*—Maulin Patel
*Attorney, Agent, or Firm*—Brinks Hofer Gilson & Lione

[57] ABSTRACT

A needle guide having a semi-compliant shell design and locating means for attachment to an ultrasound transducer. The needle guide improves over the prior art in its reduced complexity, its low-profile formed fit to the transducer, a positive guide locking feature when the needle holding pin is in the closed position, and its ease of attachment over a sterile cover. The improved design is conducive to low-cost manufacturing methods which employ materials that can be autoclaved, gas-sterilized, or liquid disinfected.

20 Claims, 3 Drawing Sheets

SEMI-COMPLIANT NEEDLE GUIDE FOR USE WITH ULTRASOUND TRANSDUCERS

BACKGROUND OF THE INVENTION

This invention relates to the use of needle guiding adapter hardware which is attached to an ultrasound transducer for real-time visual guidance of a biopsy or aspiration needle, or catheter, into the human body to a specific target location using the ultrasound system as an aid to the physician. Medical professionals are concerned with the ease and accuracy of attachment of needle guiding devices and maintenance of a sterile environment throughout a surgical procedure. In the prior art, needle guidance devices for use with ultrasound transducers have typically utilized cumbersome threaded fasteners or bulky formed metal springs which are difficult to actuate and which can trap biohazardous materials not easily cleaned by standard methods. Some examples are U.S. Pat. Nos. 5,052,396 and 4,898,178 (Wedel, et al) and U.S. Pat. No. 4,576,175 (Epstein) which all employ screw-thread type fasteners for either closing of a clamp around or direct attachment of a needle guiding device to an ultrasound transducer. U.S. Pat. No. 5,076,279 uses a dedicated formed metal spring and roller assembly for attachment.

SUMMARY OF THE INVENTION

The present invention is a needle guide comprised of a form-fitting shell of a semi-compliant material which snaps onto the ultrasound transducer adding minimal height above the surface topology of the transducer itself. The needle guide is confined to the area of the ultrasound transducer located near the patient's body, thus leaving free the handle portion of the transducer for the physician to hold and manipulate. Needle guide locating means are situated generally internal to the smooth external surface of the needle guide, thus providing sure and accurate attachment of the needle guide to the transducer in only one correct and safe orientation. Corresponding locating details are required on the transducer to accept correct attachment of the needle guide.

The material of construction offers uniformly distributed compliant behavior of the needle guide shell for simple snap-on attachment to the transducer. Further, the needle guide can be manufactured using cost effective molding or casting methods and materials rather than the more expensive machined metal devices described in the prior art. The materials of construction described in the preferred embodiment allow for the needle guide to be cleaned and sterilized by a variety of generally accepted methods including but not limited to autoclaving, gas sterilization, and liquid soak disinfection. Other even less costly materials and manufacturing methods could be used to fabricate a disposable device of the same design.

The semi-compliant shell design of this needle guide allows it to be used in conjunction with a sterile transducer cover, usually of latex or similar material, which typically fits over the transducer where it comes into contact with or in proximity of the patient. This design allows for the sterile cover to be stretched taut over the face of the transducer automatically upon attachment of the needle guide which is desirable for proper image acquisition. The compliant shell design eliminates the requirement for dedicated springs and screws of the prior art.

Because different needle sizes are often desired for various procedures, this design offers a cylindrical bore in the needle guide which can accept one of several hollow needle guiding pins each corresponding to a specific standard gage of needle.

DESCRIPTION OF A PREFERRED EMBODIMENT

Figure 1:
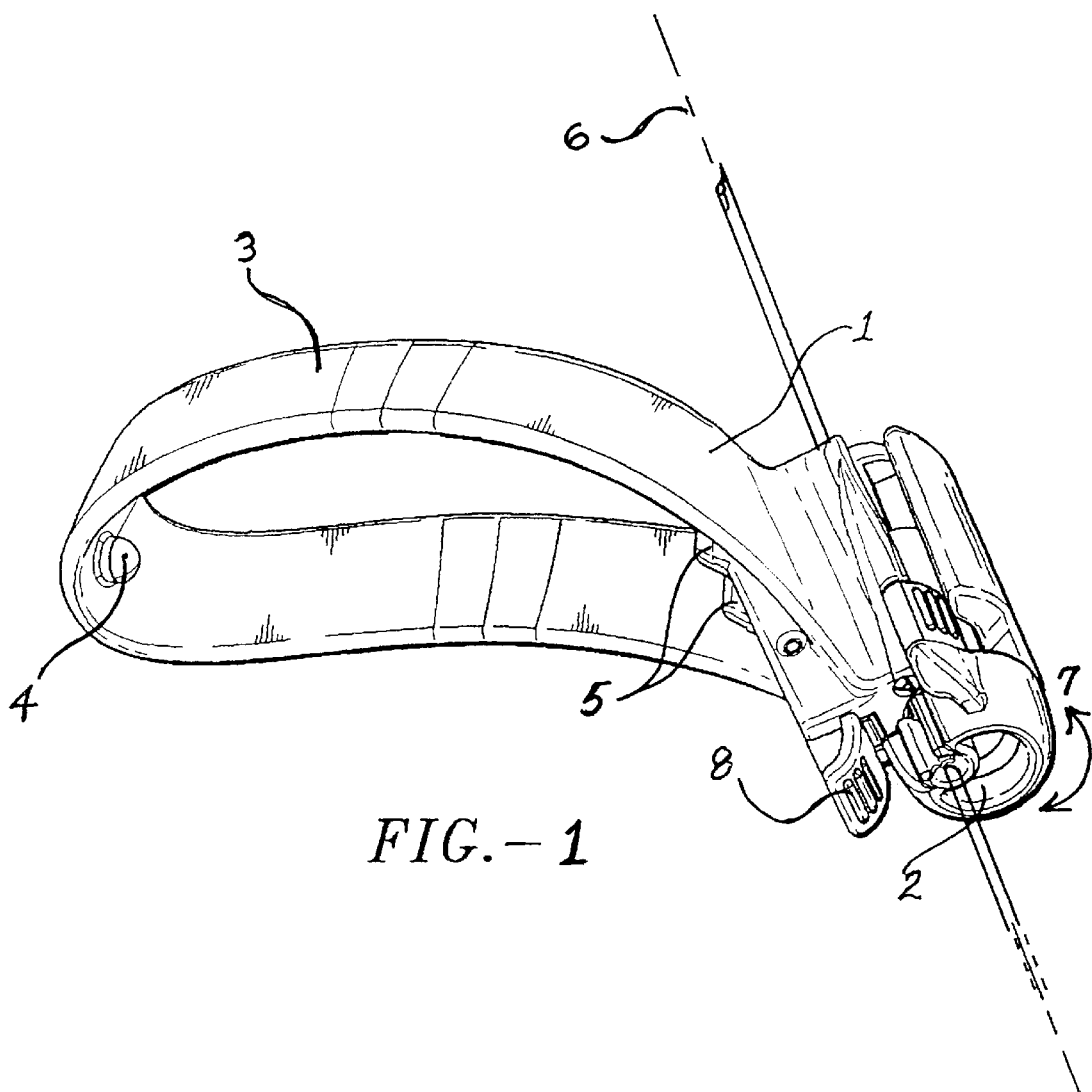
FIG. 1 is an isometric assembly view of the needle guide and hollow needle guiding pin in the cylindrical bore.

FIG. 1 illustrates the needle guide 1 assembled with a hollow needle locating and guiding pin 2 situated inside a cylindrical bore in the needle guide. The semi-compliant shell portion 3 has opposing locating details which are a single spherical shape 4 at the non-needle end, and dual linear features 5 at the needle end. The needle locating and guiding pin is assembled into the cylindrical bore of the needle guide by insertion along the axis of the needle 6. Further, the needle locating and guiding pin is rotatable about the needle axis 7 in order to allow for either full capture of the needle along the length of the locating and guiding pin with simultaneous latching of the guide to the transducer, or, removal of the assembled needle guide and transducer from a needle inserted into the patient by moving the assembly in a direction normal to the axis of the needle, with the needle exiting a slot opening created by rotating the locating and guiding pin into its open position. A spring actuated latch 8 is positively locked into attachment with the transducer when the needle locating and guiding pin is rotated closed.

Figure 2:
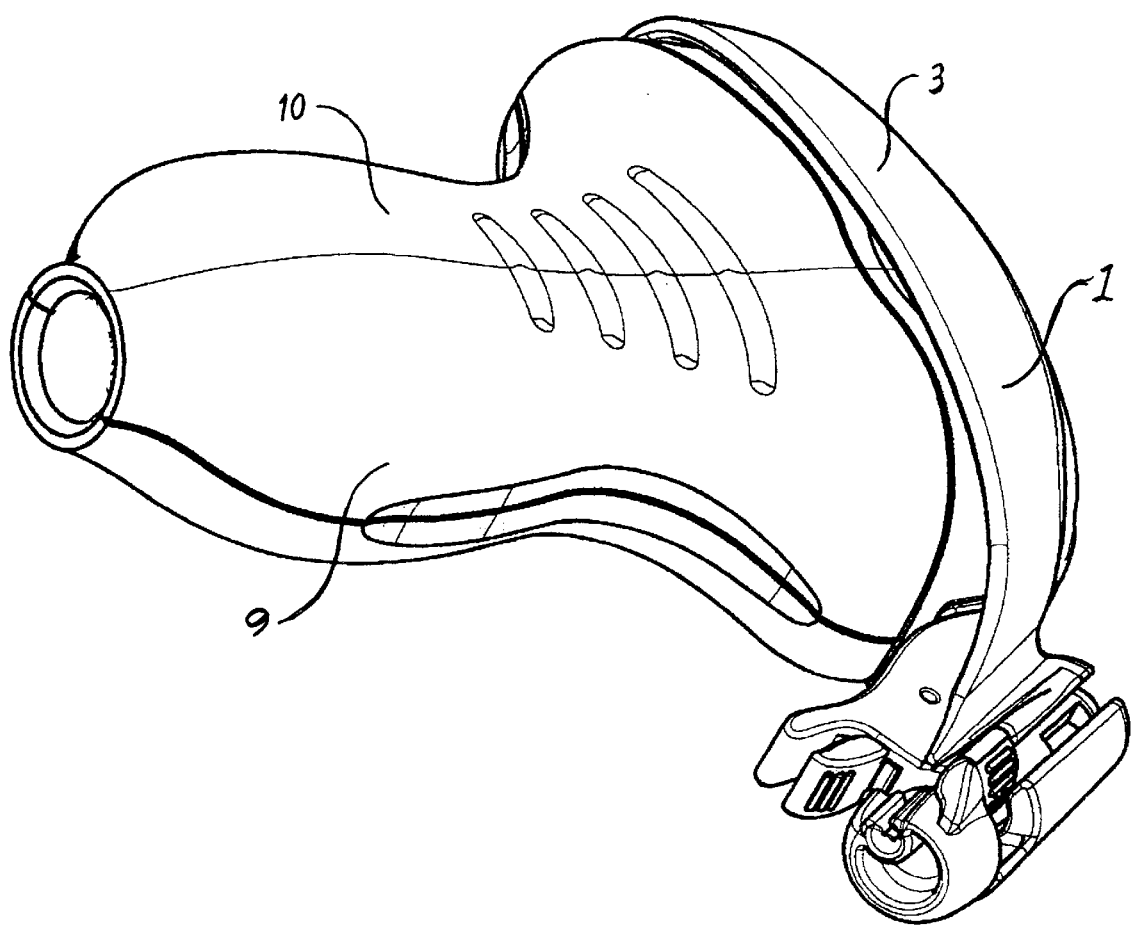
FIG. 2 is a side view of the needle guide assembly of FIG. 1 attached to an ultrasound transducer.
Figure 3:
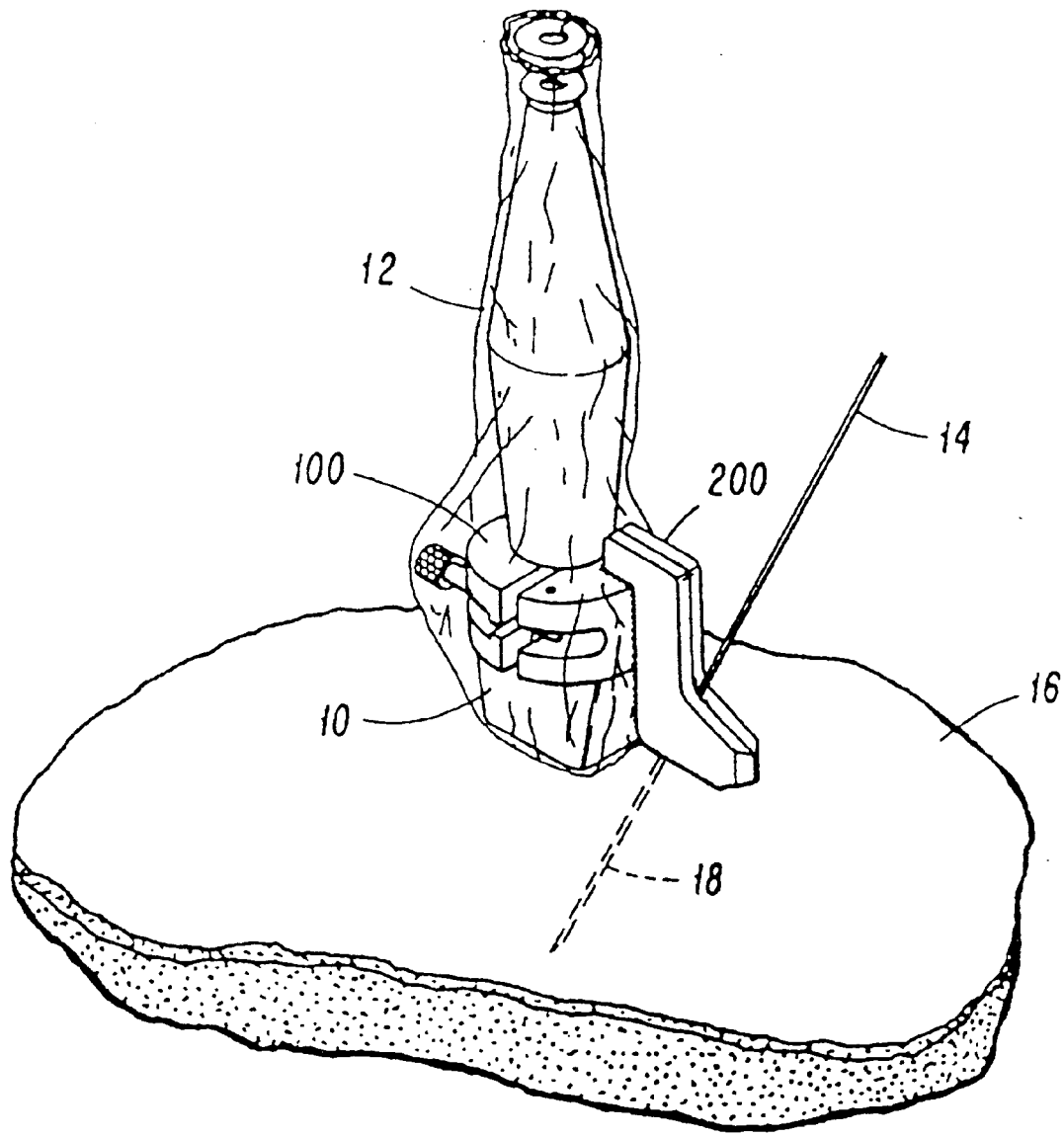
FIG. 3 is of prior art illustrating the use of bulky screw-threaded fasteners for attachment of a needle guide to an ultrasound transducer.

FIG. 2 illustrates the needle guide assembly 1 attached to an ultrasound transducer 9 . The semi-compliant shell portion 3 of the needle guide is designed to be form-fitting about the shape of the transducer, and the handle portion of the transducer 10 is left free for the physician to grip.

It is believed that the improved needle guide with its described advantages will be understood from the foregoing description, and it will be apparent that various changes may by made to the construction, form, and arrangement of the parts without departing from the spirit and scope of the invention, or sacrificing all of its material advantages, the form herein described being merely preferred or exemplary embodiments thereof. It is the intention of the appended claims to cover all such changes.

We claim:

1. A needle guide for an ultrasound transducer, the needle guide comprising:
   a form-fitting semi-compliant shell having a shape that is designed to snap-fit and encircle an end of a transducer; and
   a needle locating and guiding bore located on said semi-compliant shell.

2. The needle guide of claim 1 wherein said semi-compliant shell is made of one of molded or cast material.

3. The needle guide of claim 1 wherein said needle guiding bore is a separable needle locating and guiding pin.

4. The needle guide of claim 2 wherein said semi-compliant shell material is a polymer.

5. The needle guide of claim 1 wherein said semi-compliant shell is at least one of autoclavable, gas-sterilizable, liquid-disinfectable.

6. The needle guide of claim 3 wherein said separable needle locating and guiding pin is insertable into a cylindrical bore in the needle guide and is rotatable about the axis of the needle.

7. The needle guide of claim 6 wherein said separable needle locating and guiding pin provides two distinct positions, a closed position in which the needle is fully encased in the locating and guiding pin and an open position wherein a needle may be inserted into or removed from the needle locating and guiding bore.

8. The needle of claim 7 further comprising means for locking the needle locating and guiding pin in the closed position.

9. The needle guide of claim 7 further comprising latch for locking the needle locating and guiding pin in the closed position.

10. The needle guide of claim 9 wherein said latch is spring activated.

11. A needle guide for an ultrasound transducer, the needle guide comprising:

a closed-loop shell formed of a semi-compliant material; and a needle locating and guiding bore located on said closed-loop wherein said closed-loop shell is snap-fit onto an end of a transducer when the needle guide is to be used.

12. The assembly of claim 10 wherein said semi-compliant shell is made of one of molded or cast material.

13. The assembly of claim 10 wherein said needle guiding bore is a separable needle locating and guiding pin.

14. The assembly of claim 12 wherein said semi-compliant shell is a polymer.

15. The assembly of claim 10 wherein said semi-compliant shell is at least one of autoclavable, gas-sterilizable, liquid-disenfectable.

16. The assembly of claim 13 wherein said separable needle locating and guiding pin is insertable into a cylindrical bore in the needle guide and is rotatable about the axis of the needle.

17. The assembly of claim 16 wherein said separable needle locating and guiding pin provides two distinct positions, a closed position in which the needle is fully encased in the locating and guiding pin and an open position wherein a needle may be inserted into or removed from the needle locating and guiding bore.

18. The assembly of claim 17 further comprising means for locking the needle locating and guiding pin in the closed position.

19. The assembly of claim 17 further comprising a latch for locking the needle locating and guiding pin in the closed position.

20. The assembly of claim 18 wherein the latch is spring actuated.

* * * * *

UNITED STATES PATENT AND TRADEMARK OFFICE
CERTIFICATE OF CORRECTION

PATENT NO. : 5,924,992
DATED : July 20, 1999
INVENTOR(S) : William J. Park et al.

It is certified that error appears in the above-identified patent and that said Letters Patent is hereby corrected as shown below:

In claim 15, line 3, change "disenfectable" to --disinfectable--.

In claim 20, line 1, change "18" to --17--.

Signed and Sealed this

Twenty-sixth Day of September, 2000

Attest:

Q. TODD DICKINSON

*Attesting Officer*     *Director of Patents and Trademarks*